US009409940B2

(12) United States Patent
Xiong et al.

(10) Patent No.: US 9,409,940 B2
(45) Date of Patent: Aug. 9, 2016

(54) PREPARATION PROCESS OF ERYTHROMYCIN THIOCYANATE

(75) Inventors: Hui Xiong, Yidu (CN); Keyi Zhao, Yido (CN); Zhaozheng Deng, Yidu (CN)

(73) Assignee: HEC PHARM CO., LTD., Yidu, Hubei (CN)

( * ) Notice: Subject to any disclaimer, the term of this patent is extended or adjusted under 35 U.S.C. 154(b) by 3 days.

(21) Appl. No.: 14/240,031

(22) PCT Filed: Aug. 24, 2012

(86) PCT No.: PCT/CN2012/080554
§ 371 (c)(1),
(2), (4) Date: Feb. 21, 2014

(87) PCT Pub. No.: WO2013/029497
PCT Pub. Date: Mar. 7, 2013

(65) Prior Publication Data
US 2014/0228555 A1    Aug. 14, 2014

(30) Foreign Application Priority Data
Aug. 26, 2011 (CN) .......................... 2011 1 0248968

(51) Int. Cl.
*C07H 17/08*   (2006.01)
*C07D 407/14*  (2006.01)

(52) U.S. Cl.
CPC .............. *C07H 17/08* (2013.01); *C07D 407/14* (2013.01)

(58) Field of Classification Search
CPC ..................................................... C07H 17/08
See application file for complete search history.

(56) References Cited

U.S. PATENT DOCUMENTS 2,791,531 A * 5/1957 Bellard ........................... 514/29
2011/0184158 A1  7/2011 Liu

FOREIGN PATENT DOCUMENTS

| CN | 1099039 A  | * 2/1995  | ............ C07H 17/08 |
| CN | 101407533 A | 4/2009 | |
| GB | 1013837 | 12/1965 | |

OTHER PUBLICATIONS

English machine translation of CN1099039A above, (1995) downloaded from translationportal.epo.org.*
Li, Ping; Research of the synthesis of erythromycin thiocyanate; Chinese Journal of Veterinary Drug, 1992,vol. 26, Issue 4, p. 25-26.
English translation of the abstract of NPL-1.
Huang, A gen etc. Solubility of erythromycin in acetone-water solution; Chinese Journal of Antibiotics,1999, vol. 24, Issue 6, p. 415-416.
English translation of the abstract of NPL-3.
Determination of Erythromycin Thiocyanate and Its Related Substances by Reverse Phase-High Performance Liquid Chromatography;Chinese Pharmaceutical Journal, 2007, vol. 42, Issue 23, p. 1822-1826.
English translation of the abstract of NPL-5.
Determination of Erythromycin Thiocyanate components by Reverse Phase-High Performance Liquid Chromatography; Public Medical Forum Magazine, 2009, vol. 13, Issue 28, p. 920-921.
English translation of the abstract of NPL-7.
Zhao, Qian etc. Study on the effect of original solvent on erythromycin crystal habit and purity during its solvent-out crystallization; Chinese Journal of Antibiotics,1999, vol. 24, Issue 6, p. 410-414.
English translation of the abstract of NPL-9.
ISR
English translation of NPL-11.
Written Opinion.
English translation of NPL-13.

* cited by examiner

*Primary Examiner* — Eric Olson
(74) *Attorney, Agent, or Firm* — Kam W. Law; Squire Patton Boggs (US) LLP

(57) ABSTRACT

Disclosed herein is a method or process for preparing erythromycin thiocyanate, which belongs to the pharmaceutical field. Also disclosed herein is a method of using erythromycin or a salt thereof as a raw material, which can be dissolved in acetone or a mixed solvent containing acetone to yield erythromycin thiocyanate A as the main component and low in the content of impurities. Said erythromycin thiocyanate could be used as the raw material for preparing Azithromycin and Clarithromycin, which meets the standards made by European Union and US.

20 Claims, 8 Drawing Sheets

PREPARATION PROCESS OF ERYTHROMYCIN THIOCYANATE

CROSS-REFERENCE TO RELATED APPLICATIONS

This is a U.S. national stage application of the International Patent Application No. PCT/CN2012/080554, filed Aug. 24, 2012, which claims priority to Chinese Patent Application No. 201110248968.2, filed Aug. 26, 2011, both of which are incorporated herein by reference in their entirety.

FIELD OF THE INVENTION

The present invention relates to the field of pharmaceutical. More particularly, the invention relates to a method of preparing erythromycin thiocyanate.

BACKGROUND OF THE INVENTION

Currently, cephalosporin/semi-synthetic penicillins, fluoroquinolones and macrolides are the three first-line drugs in global anti-infective market, accounting for 80% of the anti-infective market shares. Among them, the international market share of macrolide antibiotics, led by the third generation of erythromycin, such as azithromycin, clarithromycin and roxithromycin, has increased steadily in recent years. Currently, China is the biggest manufacturer of macrolide antibiotic raw materials in the world, and the total macrolide antibiotic raw material production reaches more than 10,000 tons, which accounts for ⅔ of world total production.

Erythromycin thiocyanate, mainly used for treating infection against $G^+$ bacterial, mycoplasma and chlamydia etc., is the raw material for preparing erythromycin derivative products, such as azithromycin, clarithromycin and roxithromycin in China. Erythromycin thiocyanate becomes the third leading product in the world antibiotic market due to a large number of clinical applications of erythromycin, erythromycin derivatives and downstream products thereof. Therefore, the corresponding raw materials have a broad market space. The quality and content of erythromycin thiocyanate are measured by detecting the content of main component erythromycin A. The detection method is included in Chinese Pharmacopoeia 2005 edition. As the skilled person in this art known, although there are many manufacturers providing the raw materials, the quality of which is uneven. Chen Yue detected the content of the main component erythromycin of two samples from two different companies, and the contents were found to be 68.2%~71.8% and 73.8%~76.0% (*Determination of Erythromycin Thiocyanate and Its Related Substances by Reverse Phase-High Performance Liquid Chromatography*, Chinese Pharmaceutical Journal, 2007, 42 (23)). Wei Qi et al. reported the content of erythromycin A, the main component of erythromycin thiocyanate, was found to be 68.7%~70.5% (*Determination of Erythromycin Thiocyanate Component by Reverse Phase-High Performance Liquid Chromatography*, Public Medical Forum Magazine, 2009, 13). The skilled person in the art knows that the product with poor quality refers to the product with the content of the main component erythromycin A to be less than 72%. Erythromycin A can only be used as a veterinary drug. Even with the use of raw materials with better quality in producing the derivatives, the quality of derivatives is also uneven because of their different qualities of the raw materials. Only those products that have low cost and high quality can take up favorable competitive advantage in the market.

Erythromycin thiocyanate comprises erythromycin thiocyanate A as shown in formula I, erythromycin thiocyanate B, erythromycin thiocyanate C and other related impurities. Erythromycin thiocyanate A is the desired product and other components are all impurities. These impurities can be co-crystallized during the crystallization of erythromycin thiocyanate A or absorbed on crystal itself resulting in product with high impurity content. The level of the impurity content is not only closely related to the condition of crystallizing process, but also the kinds of solvents.

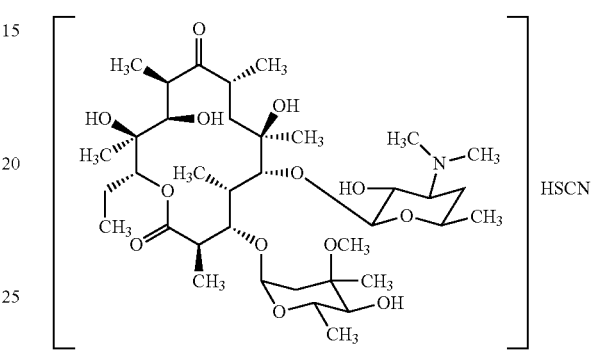

Formula I

Erythromycin thiocyanate A and the impurities like erythromycin thiocyanate B, C, D and E have different groups in molecular structure resulting in different polarities among them. Therefore, they have different solubilities in different solvents with different polarities. In order to improve the product purity, a suitable solvent system with high solubility of impurities should be selected in which the impurities would not co-crystallize with erythromycin thiocyanate A or would only precipitate a very small amount. Moreover, the kind of solvent also has an influence on the appearance of crystals. Good crystal properties favor filtration, separation, washing and drying.

In prior art, generally, solvent extraction or fixed bed adsorption was used to obtain a solution of erythromycin with butyl acetate, octanol or some mixed water-insoluble solvents. After the solution was separated, washed and filtrated, thiocyanate aqueous solution was added, stirred and mixed. Then acetic acid was added slowly to obtain the crystal slurry of erythromycin thiocyanate. The crystal slurry was centrifuged and washed to obtain wet erythromycin thiocyanate. The wet erythromycin thiocyanate was then crushed and dried to obtain erythromycin thiocyanate product. Chinese patent CN 200810179653.5 also disclosed the use of butyl acetate as a solvent.

The methods in prior art have disadvantages. The amount of erythromycin thiocyanate A in the product prepared according to the methods in prior art was less than 78%. Because of its low purity with large amount of impurities, the product cannot be used as the starting material which meets the EU and US standard for synthesizing the derivatives like azithromycin and clarithromycin.

DESCRIPTION OF THE INVENTION

For these reasons, provided herein is a method for preparing erythromycin thiocyanate. This invention provides a method for preparing erythromycin thiocyanate. The method provides the main component erythromycin thiocyanate A in high content with less impurities. Erythromycin thiocyanate A can therefore be used as a starting material that meets the EU and US standards for synthesizing azithromycin and clarithromycin. The product obtained from the method described herein has better quality, lower cost, and competitive market advantages.

In the following description, all numbers disclosed herein are approximate values, regardless whether the word "about" is used in connection therewith. The value of each number may differ by 1%, 2%, 5%, 7%, 8%, 10%, 15% or 20% etc. Whenever a number having a value N is disclosed, any number having the value N+/−1%, N+/−2%, N+/−3%, N +/−5%, N+/−7%, N+/−8%, N+/−10%, N+/−15% or 20 N+/−20% is specifically disclosed, wherein "+/−" refers to plus or minus. Whenever a numerical range with a lower limit, $R_L$, and an upper limit, $R_U$, is disclosed, any number falling within the range is specifically disclosed. In particular, the following numbers within the range are specifically disclosed: $R=R_L+ k*(R_U-R_L)$, wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined above is also specifically disclosed.

As used herein, the term "weak acid" refers to an acid with pKa value more than −1.76. In some embodiments, the weak acid is dilute acetic acid, dilute hydrochloric acid, dilute sulfuric acid, dilute sulfuric acid, dilute nitric acid.

As used herein, the term "dilute" refers to the mass fraction of an acid from 1% to 50%, or from 1% to 40%, or from 1% to 30%, or from 1% to 20%, or from 1% to 10%, or from 1% to 5%.

Guo Dunjia et al. published a publication (*The Preparation of Erythromycin Thiocyanate*, Speciality Petrochemicals, 1999 (6)). They carried out a reaction by reacting acetic acid and sodium thiocyanate with industrial eythromycin in water to obtain erythromycin thiocyanate. The molar ratio of eythromycin, HAc, and NaSCN was 1:1.30:1.15. The pH value was 7.2. The yield reached about 95%. The industrial eythromycin used in this method is much more expensive than erythromycin thiocyanate. Therefore, the manufacturers prefer to use a crude erythromycin with lots of impurities, but not the industrial erythromycin to prepare erythromycin thiocyanate. However, using the crude erythromycin in method disclosed herein will lead to product with lower content and more impurities. The purifying effect cannot be obtained. We used the optimal ratio disclosed in the publication using the crude erythromycin to refine erythromycin thiocyanate. The amount of the main component erythromycin A in the obtained dried product only reached 74.3%. The result was shown in example 7.

To achieve the above purpose, the present invention provides the following technical solutions:

Provided herein is a method for preparing erythromycin thiocyanate with high content and quality, in which erythromycin or a salt of erythromycin is used as a raw material, and acetone or a mixed solvent comprising acetone is used as the reaction solvent or crystallization solvent.

The method disclosed herein comprises the following steps:

a) dissolving the erythromycin or erythromycin salt or a mixture thereof in the acetone or the mixed solvent under alkaline condition to form a solution of the erythromycin or erythromycin salt;

b) adding a thiocyanate salt into the solution; and c) adjusting the pH of the solution to neutral to slightly acidic or neutral to slightly alkaline, and forming crystals.

The erythromycin or erythromycin salt disclosed herein used as a raw material could be crude product or refined product prepared by other methods in which the content does not meet the content of the present invention. The erythromycin salt disclosed herein is erythromycin thiocyanate or erythromycin lactate.

The content of the acetone in the mixed solvent is more than 40%, or more than 50%, or more than 60%, or more than 70%, or more than 80%, or more than 90% by volume. The other solvent could be an alcohol solvent, an ether solvent, a halogenated solvent, an ester solvent, a ketone solvent other than acetone, water or a combination thereof; wherein the alcohol solvent is a C1-C6 alcohol, such as methanol, ethanol, n-propanol, isopropanol, n-butanol or a combination thereof; the ether solvent is tetrahydrofuran, diethyl ether, dioxane, methyl tert-butyl ether, dimethoxyethane, diethylene glycol dimethyl ether, triethylene glycol dimethyl ether or a combination thereof; the halogenated solvent is dichloromethane, 1,2-dichloroethane, chloroform or a combination thereof; the ester solvent is ethyl acetate, isopropyl acetate, butyl acetate or a combination thereof; and the ketone solvent is butanone.

The alkaline condition refers to the pH of the erythromycin solution from 7.5 to 11.0, or from 8.5 to 10.0, or from 9.0 to 9.5. Sodium hydroxide, potassium hydroxide, ammonium hydroxide, sodium carbonate, potassium carbonate, sodium bicarbonate, potassium bicarbonate or a combination thereof could be used as a pH adjusting agent In step a, the amount of the erythromycin or erythromycin salt in the solution is from 5% to 35%, or from 10% to 30%, or from 10% to 25%.

The thiocyanate salt is sodium thiocyanate, potassium thiocyanate, ammonium thiocyanate or a combination thereof. The molar ratio of the thiocyanate salt and the erythromycin or erythromycin salt is from 0.1:1 to 5:1, or from 0.1:1 to 3:1, or from 0.2:1 to 2:1.

In step c, the pH of the solution is from 6.0 to 8.0. In some embodiments, the pH is from 6.0 to 7.5. In some embodiments, the pH is from 7.0 to 7.5. Weak acid could be used as a pH adjusting agent. The weak acid disclosed herein is an inorganic acid, an organic acid or a combination thereof, or the weak acid is dilute acetic acid, dilute hydrochloric acid, dilute sulfuric acid, dilute phosphoric acid, dilute nitric acid or a combination thereof.

In the method described herein, the temperature is decreased gradiently, and the temperature of the solution in step a and step b is kept at from 30° C. to 60° C., or from 35° C. to 55° C., or from 35° C. to 50° C. In some embodiments, the temperature is from 40° C. to 50° C. In some embodiments, the temperature is from 40° C. to 45° C. The temperature in step c is decreased to −10° C. to 15° C., or 0° C. to 10° C. In some embodiments, the temperature is from 0° C. to 5° C. In some embodiments, the temperature is from 5° C. to 10° C. In some embodiments, the temperature is 0° C., or 5° C., or 10° C.

In some embodiments, the solution is filtered before adding the thiocyanate salt if there are insoluble solid impurities in the solution. However, this step is not necessary.

The crystals formed in the present method can be collected with methods that are well known to the skilled person in the art, such as separation, washing and drying. Separation described herein can be performed by commonly used equipments in the field, such as centrifuges, filtration equipment, pressure filter and so on.

The erythromycin thiocyanate crystals separated by centrifugation can be washed by water, organic solvent or a combination thereof, wherein the organic solvent is ethyl acetate, acetone, butyl acetate, octanol or a combination thereof. The residue solvent can be removed by drying.

In the dried erythromycin thiocyanate crystal obtained according to the present method, the content of the main component erythromycin A is about more than 78%, or about more than 79%, or about more than 80%, or about more than 81%, or about more than 82%, or about more than 83%, or about more than 84%, or about more than 85% (detected by HPLC).

The advantages of the method provided herein are as follows:
1. Using acetone instead of solvent butyl acetate or water etc. disclosed in prior art is better. The product obtained according to the present method has high purity. The amount of erythromycin A in the erythromycin thiocyanate is about more than 78%, or about more than 79%, or about more than 80%, or about more than 81%, or about more than 82%, or about more than 83%, or about more than 84%, or about more than 85%. Using these as raw materials to produce azithromycin etc. would lead to better quality and yield.
2. The concentration of the erythromycin or erythromycin salt dissolved in acetone is up to 20%. The amount of acetone used is less than 25% of the amount of butyl acetate or water (butyl acetate or water etc. can only dissolve less than 5%). Moreover, acetone has a low boiling point and can be recovered. The cost of manufacture is lowered, as well as producing no waste water to contaminate the environment.
3. Acetone is a low toxicity solvent, having lower toxicity than butyl acetate, and is less harmful to workers.

EXAMPLES

Figure 1:
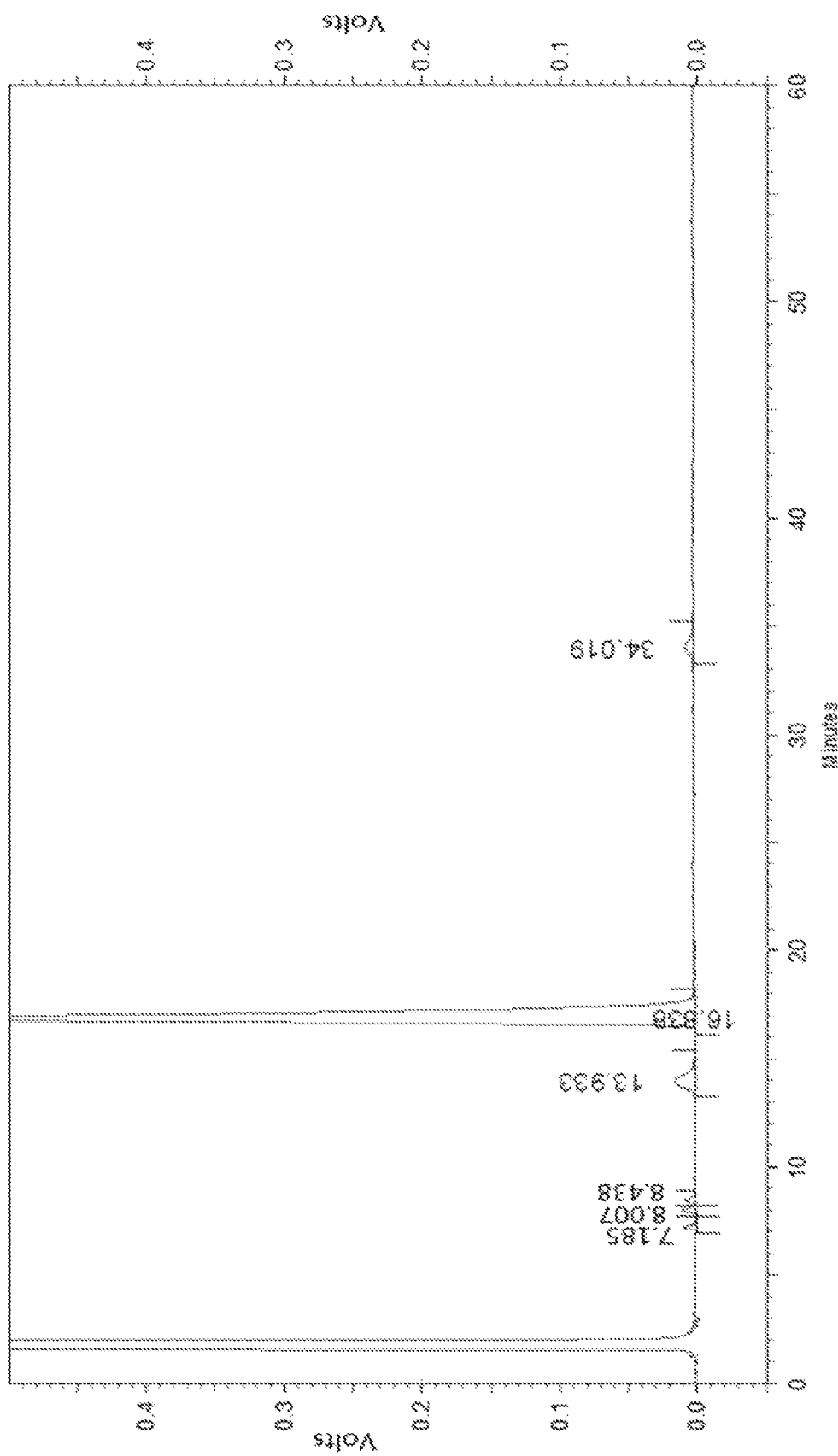
FIG. 1 depicts the HPLC spectrum of erythromycin thiocyanate A obtained from example 1.
Figure 2:
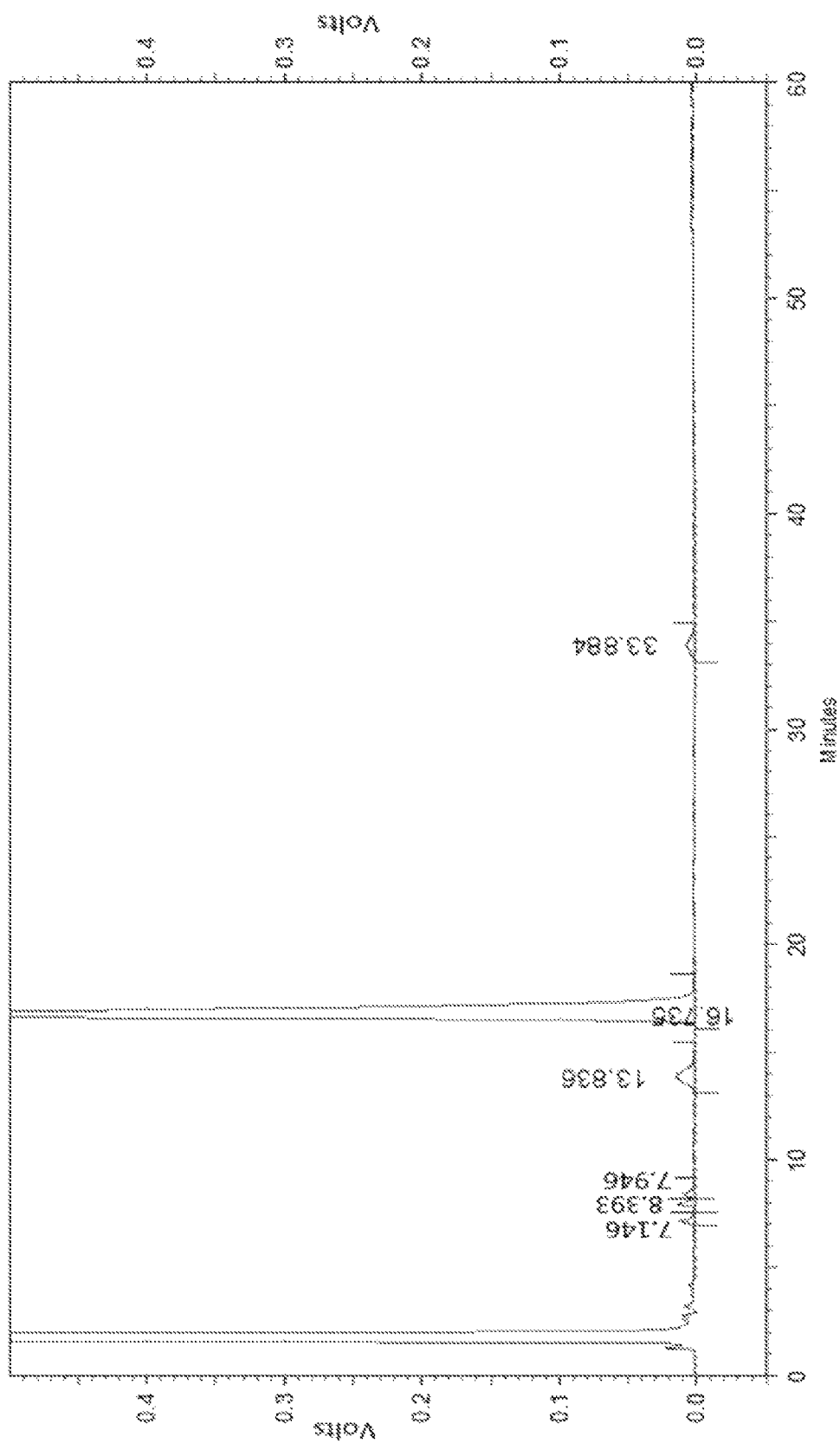
FIG. 2 depicts the HPLC spectrum of erythromycin thiocyanate A obtained from example 2.
Figure 3:
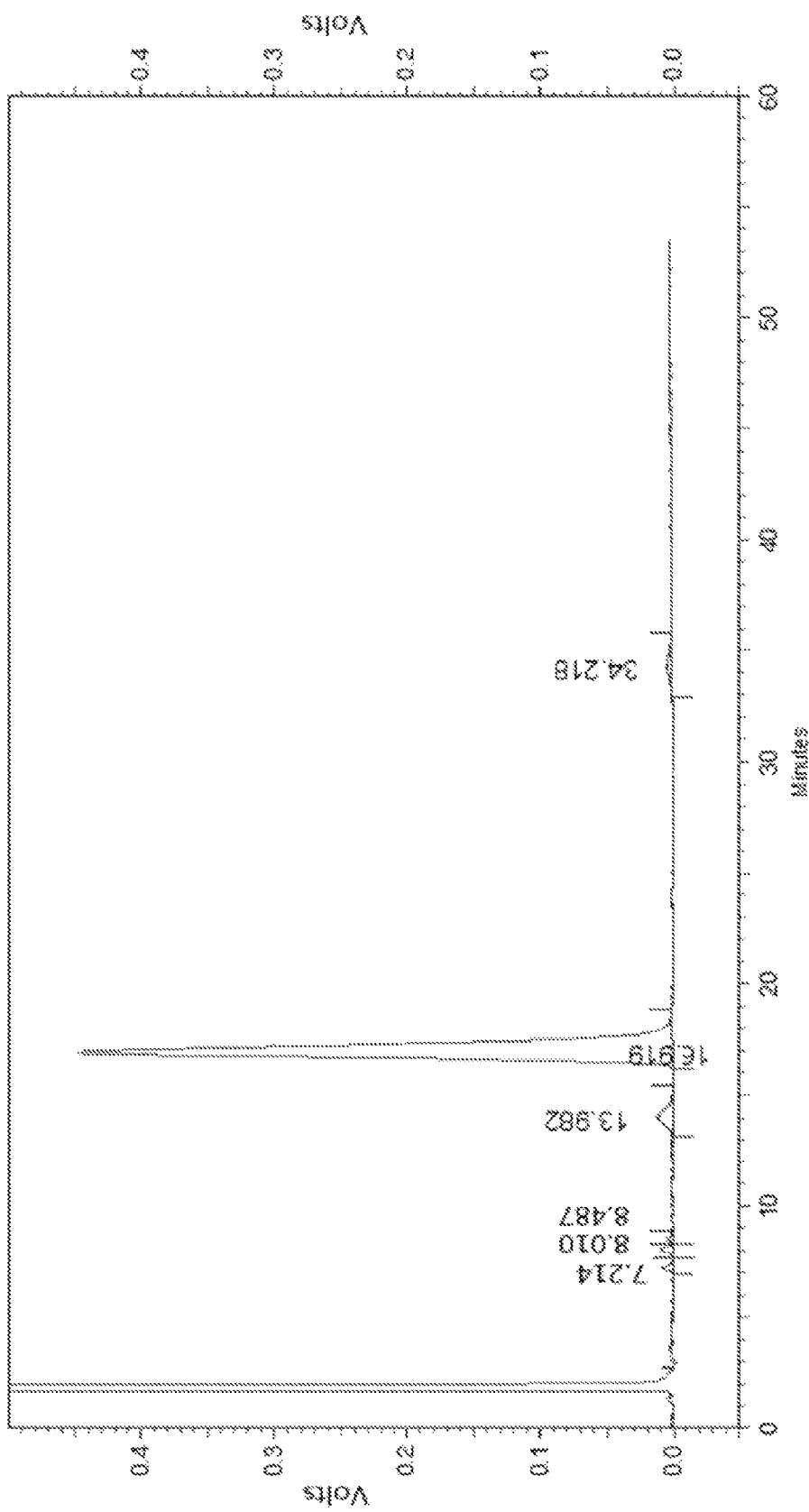
FIG. 3 depicts the HPLC spectrum of erythromycin thiocyanate A obtained from example 3.
Figure 4:
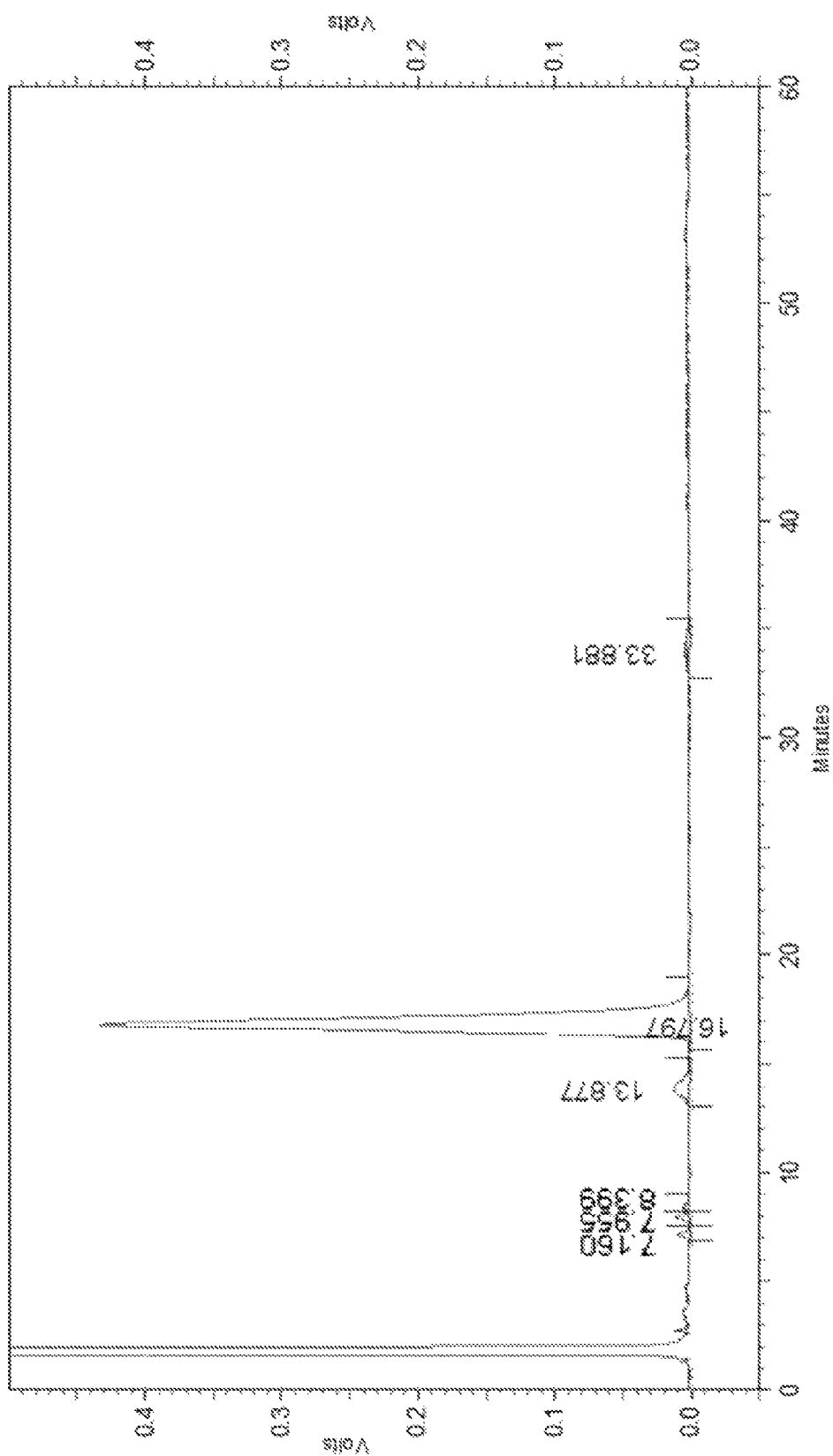
FIG. 4 depicts the HPLC spectrum of erythromycin thiocyanate A obtained from example 4.
Figure 5:
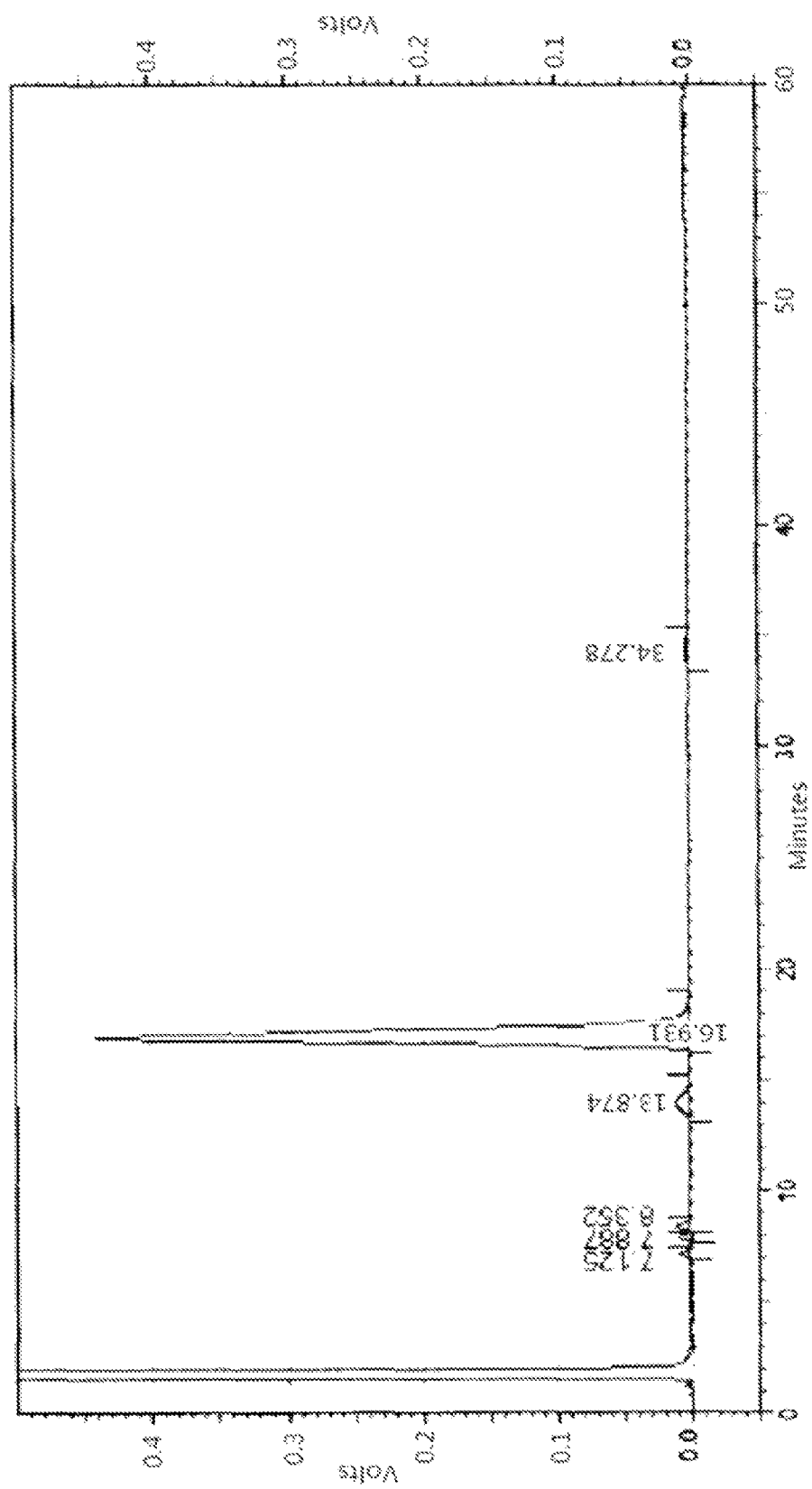
FIG. 5 depicts the HPLC spectrum of erythromycin thiocyanate A obtained from example 5.
Figure 6:
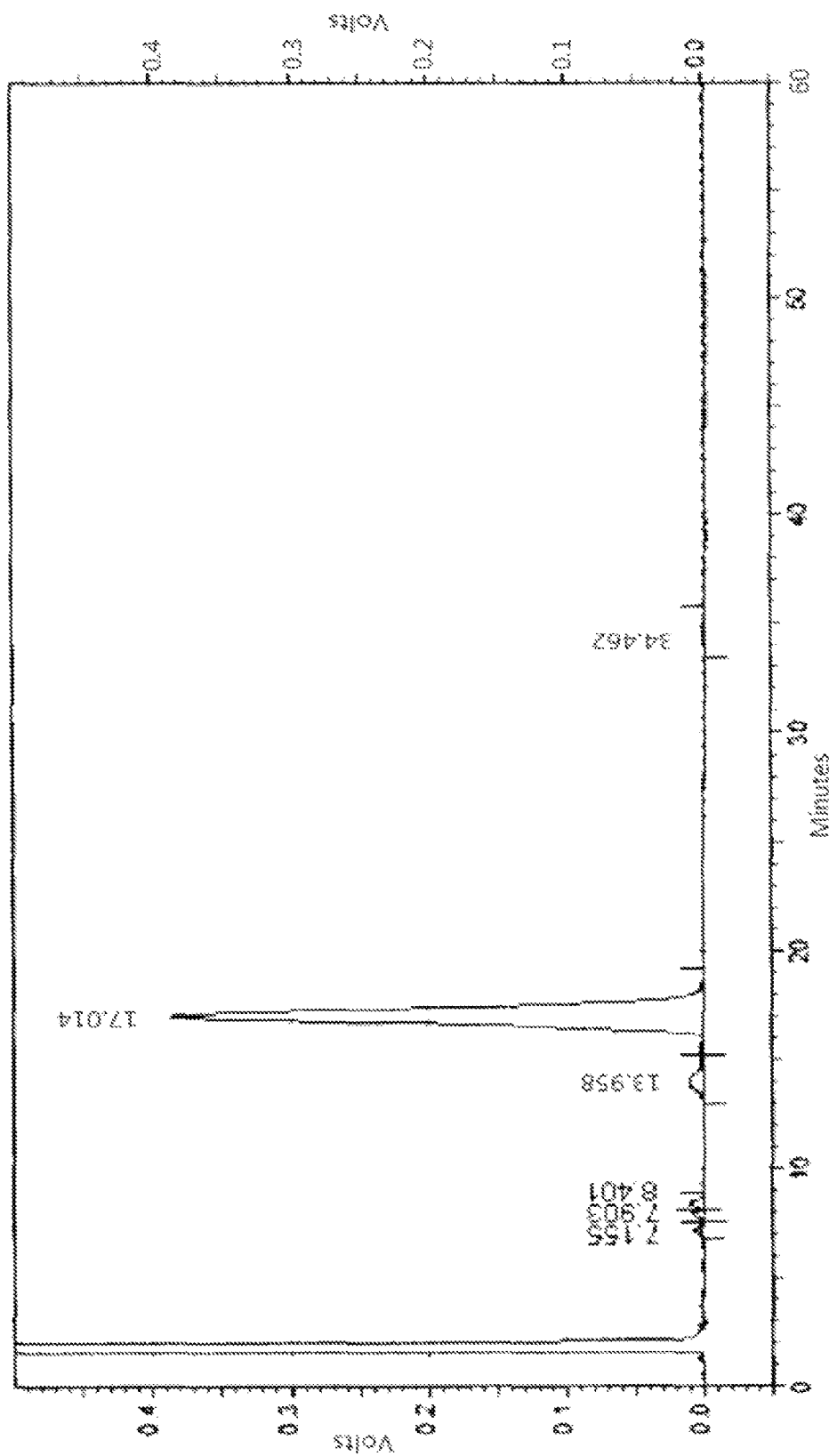
FIG. 6 depicts the HPLC spectrum of erythromycin thiocyanate A obtained from example 6.
Figure 7:
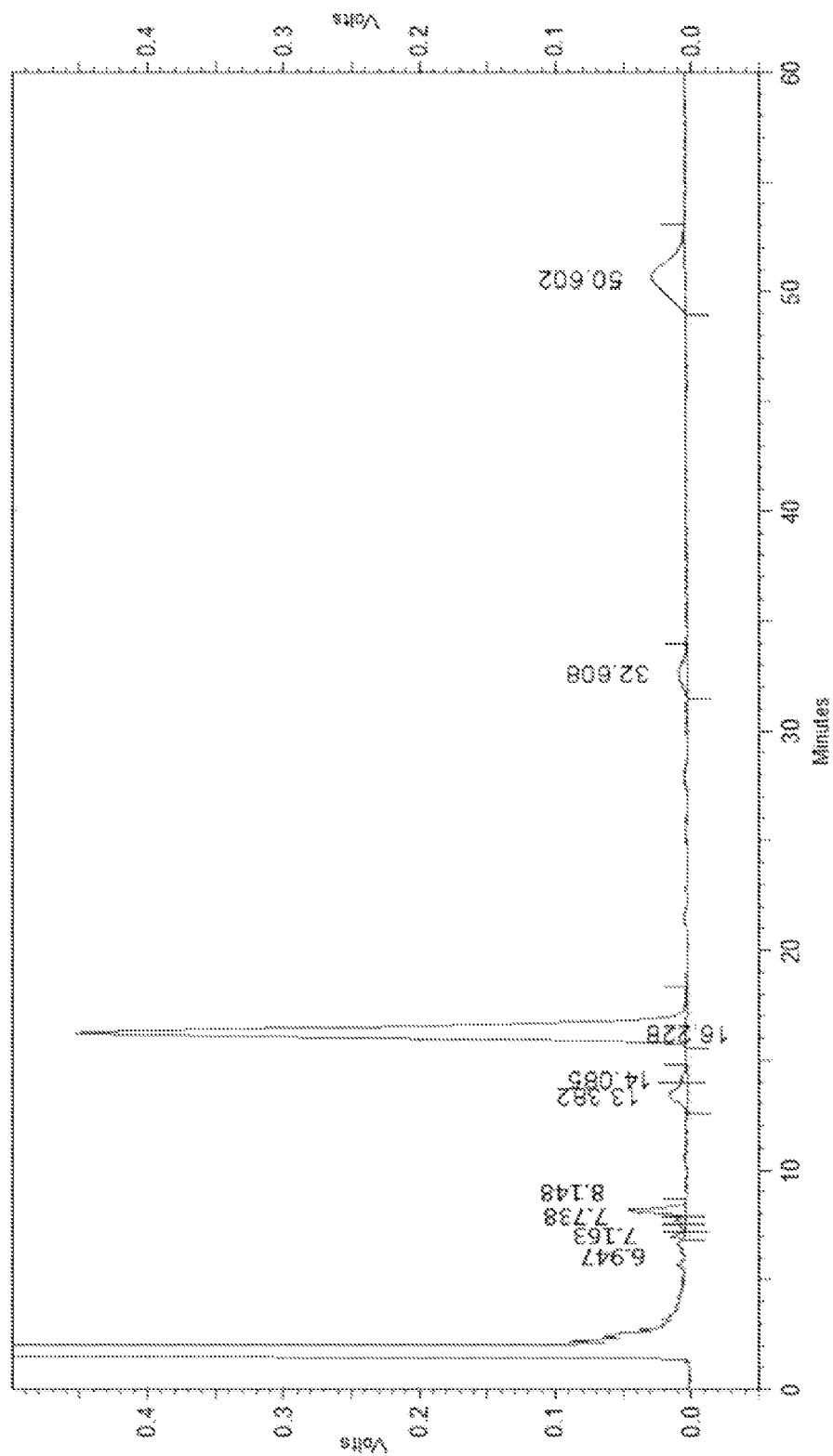
FIG. 7 depicts the HPLC spectrum of erythromycin thiocyanate A obtained from example 7.

The present invention discloses a method for refining or preparing erythromycin thiocyanate. The skilled person in the art can learn from the present invention and improve the method parameters appropriately. It should be noted that it can be readily apparent to those of ordinary skilled in the art that certain modifications may be made thereto within the scope of the invention. Some preferred embodiments of the invention are disclosed herein. Obviously, a skilled artisan can make any alterations, changes or a combination thereof appropriately to implement and apply the present invention without departing from the content, spirit and scope of the present invention. The reagents used in the present invention could be bought on market or prepared according to the method disclosed in the present invention.

In order to make the skilled person in the art having a better understanding of the technical solutions of the present invention, provided herein are detailed examples as shown below.

Example 1

Crude erythromycin (100 g) was added into acetone (600 mL), heated to 35° C. in a water bath and adjusted to pH 8.5. Filtrate was obtained after filtration and the temperature of filtrate was kept at 35° C. Then sodium thiocyanate was added into the filtrate and stirred to dissolve. The molar ratio of sodium thiocyanate and erythromycin was 2:1. The mixture was adjusted to pH 6.0 with acetic acid, cooled to 10° C. slowly and kept for 15 minutes. Then precipitate was separated, washed with pure water (100 mL), crushed and dried to obtain erythromycin thiocyanate. The amount of the main component dried erythromycin A was 85.1% (detected by HPLC).

Example 2

Crude erythromycin thiocyanate (150 g) was added into acetone (600 mL), heated to 45° C. in a water bath and adjusted to pH 10.0. Filtrate was obtained after filtration and the temperature of filtrate was kept at 45° C. Then potassium thiocyanate was added into the filtrate, and stirred to dissolve. The molar ratio of potassium thiocyanate and erythromycin thiocyanate was 0.2:1. The mixture was adjusted to pH 7.5 with diluted hydrochloric acid, cooled to 0° C. slowly and kept for 15 minutes. Then precipitate was separated, washed with pure water (100 mL), crushed and dried to obtain erythromycin thiocyanate. The amount of the main component dried erythromycin A was 84.7% (detected by HPLC).

Example 3

Crude erythromycin lactate (150 g) was added into acetone (600 mL), heated to 40° C. in a water bath and adjusted to pH 9.0. Filtrate was obtained after filtration and the temperature of filtrate was kept at 45° C. Then ammonium thiocyanate was added into the filtrate and stirred to dissolve. The molar ratio of ammonium thiocyanate and erythromycin lactate was 2:1. The mixture was adjusted to pH 7.5 with diluted hydrochloric acid, cooled to 5° C. slowly and kept for 15 minutes. Then precipitate was separated, washed with pure water (100 mL), crushed and dried to obtain erythromycin thiocyanate. The amount of the main component dried erythromycin A was 84.9% (detected by HPLC).

Example 4

A mixture of erythromycin and other impurities (150 g) was added into acetone (600 mL), heated to 45° C. in a water bath and adjusted to pH 9.5. Filtrate was obtained after filtration and the temperature of filtrate was kept at 45° C. Then ammonium thiocyanate was added into the filtrate and stirred to dissolve. The molar ratio of ammonium thiocyanate and erythromycin was 2:1. The mixture was adjusted to pH 7.0 with dilute sulphuric acid, cooled to 10° C. slowly and kept for 15 minutes. Then precipitate was separated, washed with pure water (100 mL), crushed and dried to obtain erythromycin thiocyanate. The amount of the main component dried erythromycin A was 85.0% (detected by HPLC).

Example 5

A mixture of erythromycin thiocyanate and other impurities (150 g) was added into acetone (600 mL), heated to 47° C. in a water bath and adjusted to pH 10.0. Filtrate was obtained after filtration and the temperature of filtrate was kept at 47° C. Then potassium thiocyanate was added into the solution and stirred to dissolve. The molar ratio of potassium thiocyanate and erythromycin thiocyanate was 0.2:1. The mixture was adjusted to pH 7.5 with dilute nitric acid, cooled to 0° C. slowly and kept for 15 minutes. Then precipitate was separated, washed with acetone (100 mL), crushed and dried to obtain erythromycin thiocyanate. The amount of the main component dried erythromycin A was 84.9% (detected by HPLC).

Example 6

A mixture of erythromycin lactate and other impurities (150 g) was added into acetone (600 mL), heated to 40° C. in a water bath and adjusted to pH 9.5 with dropwise addition of potassium hydroxide solution. Filtrate was obtained after filtration and the temperature of filtrate was kept at 45° C. Then ammonium thiocyanate was added into the filtrate and stirred to dissolve. The molar ratio of ammonium thiocyanate and erythromycin lactate was 2:1. The mixture was adjusted to pH 7.5 with diluted hydrochloric acid, cooled to 5° C. slowly and kept for 15 minutes. Then precipitate was separated, washed with pure water (100 mL), crushed and dried to obtain erythromycin thiocyanate. The amount the main component dried erythromycin A was 84.6% (detected by HPLC).

Example 7

Crude erythromycin (a mixture of erythromycin and other impurities) (30 g) was added into pure water (300 mL). The solution was stirred. Glacial acetic acid 20% (9.9 mL) was slowly added dropwise to the solution followed by stirring for 20 minutes. Then the mixture was filtered to remove the insoluble impurities in crude. Sodium thiocyanate solution 20% (18.4 mL, 0.038 mol) was added dropwise into the filtrate. The solution was stirred, adjusted to pH 7.2, and allowed to react for 1.5 h. After precipitation, the mixture was cooled for crystallization. The precipitate was filtered and washed with pure water for 3 times, and then dried to obtain erythromycin thiocyanate. The amount of the main component dried erythromycin A was 74.3% (detected by HPLC).

Example 8

HPLC Detecting Method and Results

The product obtained in the above examples was detected by HPLC chromatography with external standard method. The results were depicted in FIG. 1 to FIG. 6. The detecting methods are as follows:

Chromatography System: Agilent 1200; Column: XBridge C8 4.6 mm×250 mm, 5 μm; Detector: UV detector; Wavelength: 215 nm; Injection volume: 20 μl; Column temperature: 40° C.; Mobile phase: aqueous ammonia/acetonitrile=57/43, diluted 500 times; Flow rate: 1.0 ml/min; Recording time: 60 minutes.

Solution A: a mixture of pure water and acetonitrile in a ratio of 57:43.

Standard solution: standard erythromycin A (80 mg) was accurately weighted and added into a volumetric flask (25 mL). Acetonitrile (2 mL) was added to form a solution. Then the solution was diluted to 25 mL with Solution A, shaken, and filtered with 0.45 μm microporous membrane.

Sample solution: erythromycin thiocyanate (200 mg) was accurately weighted and added into a volumetric flask (50 ml), and acetonitrile (4 mL) was added to form a solution. Then the solution was diluted to 50 ml with Solution A, shaken, and filtered with 0.45 μm microporous membrane.

Figure 8:
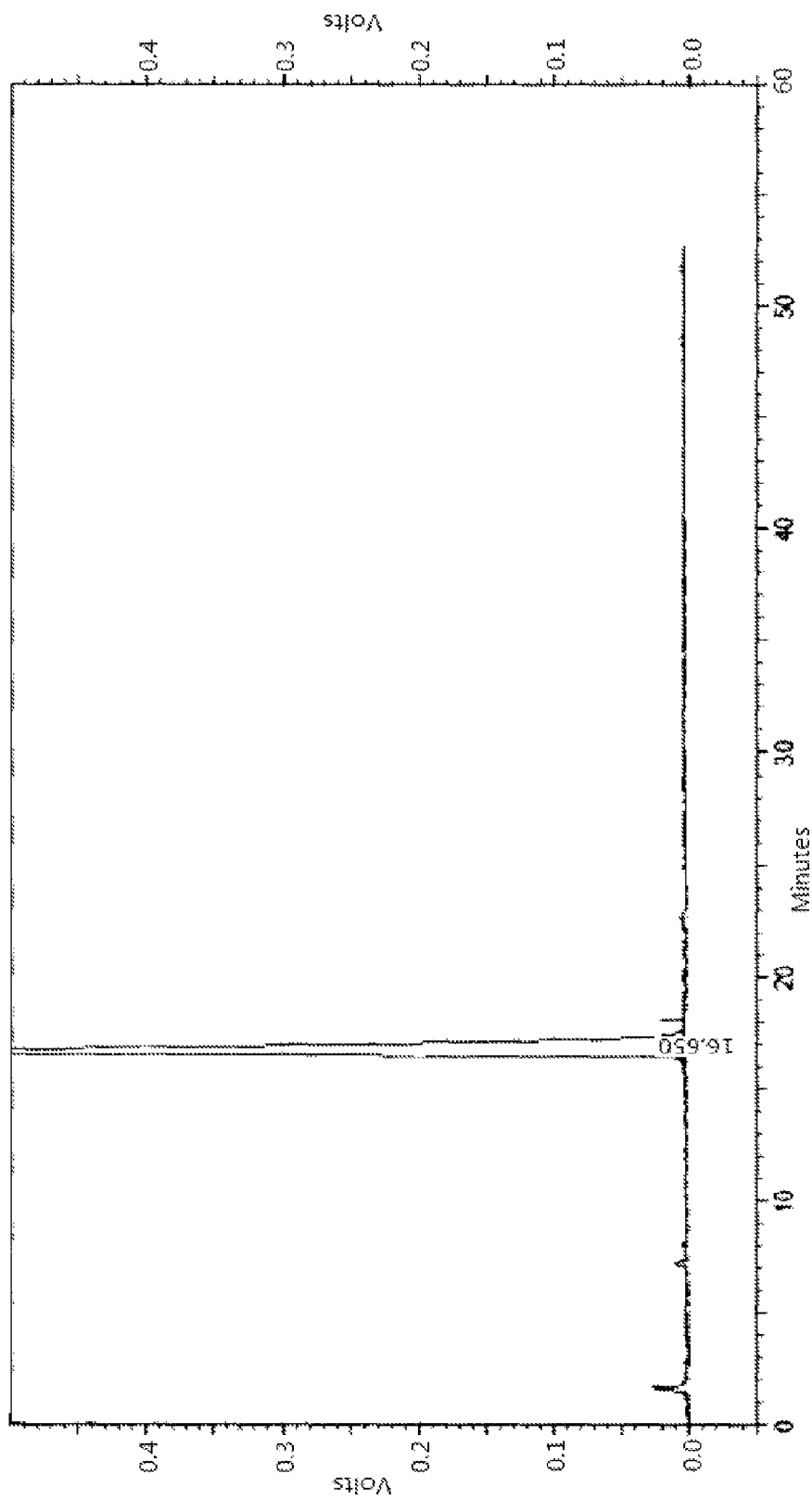
FIG. 8 depicts the HPLC spectrum of standard erythromycin thiocyanate A in example 8.

In FIG. 8, the peak with retention time (RT) at about 17 minutes is the corresponding peak of standard erythromycin A.

The amount of the main component erythromycin A was calculated with the following methods:

$$\text{Erythromycin } A \text{ (dry product) \%} = (A_t \times M_s \times V_t \times P_s\%) \\ 100\% / (A_s \times M_t \times V_s)/(1-\text{Wt \%});$$

Wherein:
At means the peak area of erythromycin A in sample solution;
As means the average peak area of erythromycin A in standard solution with two injections;
Ms means mass of standard products;
Mt means mass of sample;
Vs means volume of standard solution;
Vt means volume of sample solution;
Ps % means purity of erythromycin A in standard erythromycin;
Wt % means water content of sample.

Those illustrative embodiments are the preferred embodiments of the present invention. It should be noted that, without departing from the principles of the invention provided, many adaptations and modifications such as the change of the amount of crystallization solvent, adjustment of temperature within a certain range, crystallization time, amount of acid or alkali, or amount of thiocyanate salt etc. may be made within the scope of the invention in accordance with the common general knowledge of those skilled in this art.

What is claimed is:

1. A method for preparing erythromycin thiocyanate, comprising:
    a) dissolving erythromycin or an erythromycin salt or a mixture thereof in acetone or a mixed solvent comprising acetone under alkaline condition to form a solution of the erythromycin or erythromycin salt;
    b) adding a thiocyanate salt into the solution under alkaline condition;
    c) adjusting the pH of the solution to from 6.0 to 8.0; and
    d) forming crystals of erythromycin thiocyanate by cooling the solution to a temperature from 0° C. to 10° C.,
    wherein the solution in step a and step b is kept at a temperature from 35° C. to 50° C. and
    wherein the content of erythromycin thiocyanate A in the crystals of erythromycin thiocyanate is more than 79%, based on the total weight of the erythromycin thiocyanate.

2. The method of claim 1, wherein the erythromycin salt is erythromycin thiocyanate or erythromycin lactate.

3. The method of claim 1, wherein the alkaline condition is that the pH of the solution is from 7.5 to 11.0, or from 8.5 to 10.0, or from 9.0 to 9.5.

4. The method of claim 3, wherein sodium hydroxide, potassium hydroxide, ammonium hydroxide, sodium carbonate, potassium carbonate, sodium bicarbonate, potassium bicarbonate or a combination thereof is used to adjust the pH in step a.

5. The method of claim 1, wherein the amount of the erythromycin or erythromycin salt in step a is from 5% to 35%, or from 10% to 30%, or from 10% to 25%.

6. The method of claim 1, wherein the content of the acetone in the mixed solvent is more than 40%, or more than 50%, or more than 60%, or more than 70%, or more than 80%, or more than 90% by volume; wherein the other solvent is an alcohol solvent, an ether solvent, a halogenated solvent, an ester solvent, a ketone solvent other than acetone, water or a combination thereof; wherein the alcohol solvent is a $C_1$-$C_6$ alcohol; the ether solvent is tetrahydrofuran, diethyl ether, dioxane, methyl tert-butyl ether, dimethoxyethane, diethylene glycol dimethyl ether, triethylene glycol dimethyl ether or a combination thereof; the halogenated solvent is dichloromethane, 1,2-dichloroethane, chloroform or a combination thereof; the ester solvent is ethyl acetate, isopropyl acetate, butyl acetate or a combination thereof; and the ketone solvent is butanone.

7. The method of claim 1, wherein the thiocyanate salt is sodium thiocyanate, potassium thiocyanate, ammonium thiocyanate or a combination thereof, the molar ratio of the thiocyanate salt and the erythromycin or erythromycin salt is from 0.1:1 to 5:1, or from 0.1:1 to 3:1, or from 0.2:1 to 2:1.

8. The method of claim 1, wherein the pH of the solution in step c is adjusted to from 6.0 to 7.5, or from 7.0 to 7.5 by a weak acid, and wherein the weak acid is an inorganic acid, an organic acid or a combination thereof, or the weak acid is dilute acetic acid, dilute hydrochloric acid, dilute sulfuric acid, dilute phosphoric acid, dilute nitric acid or a combination thereof.

9. The method of claim 1, wherein the solution in step a and step b is kept at a temperature from 40° C. to 50° C., or from 40° C. to 45° C.; and wherein the temperature of the solution in step d is decreased to from 0° C. to 5° C.

10. The method of claim 1, wherein the solution is filtered to remove insoluble solid impurities before adding the thiocyanate salt into the solution in step b.

11. The method of claim 1, wherein the content of erythromycin thiocyanate A in the crystals of erythromycin thiocyanate is more than 80%, based on the total weight of the erythromycin thiocyanate.

12. The method of claim 2, wherein the alkaline condition in step a is that the pH of the solution is from 7.5 to 11.0, or from 8.5 to 10.0, or from 9.0 to 9.5.

13. The method of claim 12, wherein sodium hydroxide, potassium hydroxide, ammonium hydroxide, sodium carbonate, potassium carbonate, sodium bicarbonate, potassium bicarbonate or a combination thereof is used to adjust the pH in step a.

14. The method of claim 13, wherein the amount of the erythromycin salt in step a is from 5% to 35%, or from 10% to 30%, or 10% to 25%.

15. The method of claim 14, wherein the content of the acetone in the mixed solvent is more than 40%, or more than 50%, or more than 60%, or more than 70%, or more than 80%, or more than 90% by volume; wherein the other solvent is an alcohol solvent, an ether solvent, a halogenated solvent, an ester solvent, a ketone solvent other than acetone, water or a combination thereof; and wherein the alcohol solvent is a $C_1$-$C_6$ alcohol; the ether solvent is tetrahydrofuran, diethyl ether, dioxane, methyl tert-butyl ether, dimethoxyethane, diethylene glycol dimethyl ether, triethylene glycol dimethyl ether or a combination thereof; the halogenated solvent is dichloromethane, 1,2-dichloroethane, chloroform or a combination thereof; the ester solvent is ethyl acetate, isopropyl acetate, butyl acetate or a combination thereof; and the ketone solvent is butanone.

16. The method of claim 15, wherein the thiocyanate salt is sodium thiocyanate, potassium thiocyanate, ammonium thiocyanate or a combination thereof; and wherein the molar ratio of the thiocyanate salt and the erythromycin salt is from 0.1:1 to 5:1, or from 0.1:1 to 3:1, or from 0.2:1 to 2:1.

17. The method of claim 16, wherein the pH of the solution in step c is adjusted to from 6.0 to 7.5, or from 7.0 to 7.5 by a weak acid.

18. The method of claim 17, wherein the temperature of the solution in step a and step b is kept in a temperature ranging from 40° C. to 50° C., or from 40° C. to 45° C.; and wherein the temperature of the solution in step d is decreased to a temperature ranging from 0° C. to 5° C.

19. The method of claim 18, wherein the solution is filtered to remove insoluble solid impurities before adding the thiocyanate salt.

20. The method of claim 17, wherein the weak acid is an inorganic acid, an organic acid or a combination thereof, or the weak acid is dilute acetic acid, dilute hydrochloric acid, dilute sulfuric acid, dilute phosphoric acid, dilute nitric acid or a combination thereof.

* * * * *